United States Patent [19]

Picard et al.

[11] Patent Number: 4,923,861

[45] Date of Patent: May 8, 1990

[54] 6-(2-(2-(SUBSTITUTED AMINO)-3-QUINOLINYL) ETHENYL AND ETHYL) TETRAHYDRO-4-HYDROXYPYRAN-2-ONE INHIBITORS OF CHOLESTEROL BIOSYNTHESIS

[75] Inventors: Joseph A. Picard, Ann Arbor; Drago R. Sliskovic, Ypsilanti, both of Mich.

[73] Assignee: Warner-Lambert Company, Morris Plains, N.J.

[21] Appl. No.: 307,442

[22] Filed: Feb. 7, 1989

[51] Int. Cl.$^5$ .................. C07D 417/00; C07D 413/00; C07D 215/60; C07D 215/38

[52] U.S. Cl. .............................. 514/227.8; 514/231.5; 514/311; 514/315; 544/62; 544/128; 544/363; 548/153; 548/159

[58] Field of Search ................ 546/159, 153; 514/311, 514/227.8, 231.5, 315; 544/62, 128, 363

[56] References Cited

U.S. PATENT DOCUMENTS 4,761,419  8/1988  Picard et al. .................. 514/311

Primary Examiner—Anton H. Sutto
Assistant Examiner—E. C. Ward
Attorney, Agent, or Firm—Francis J. Tinney

[57] ABSTRACT

Novel 6-[2-[2-(substituted amino)-3-quinolinyl]-ethenyl and ethyl]tetrahydro-4-hydroxypyran-2-ones and/or oxides and the corresponding dihydroxy ring opened acids and esters are described, as well as methods for the preparation and pharmaceutical compositions of same, which are useful as inhibitors of the enzyme 3-hydroxy-3-methylglutaryl-coenzyme A reductase (HMG-CoA reductase) and are thus useful hypolipidemic and hypocholesterolemic agents.

6 Claims, No Drawings

6-(2-(2-(SUBSTITUTED AMINO)-3-QUINOLINYL) ETHENYL AND ETHYL) TETRAHYDRO-4-HYDROXYPYRAN-2-ONE INHIBITORS OF CHOLESTEROL BIOSYNTHESIS

BACKGROUND OF THE INVENTION

The present invention relates to novel 6-[2-[2(substituted amino)-3-quinolinyl]ethenyl and ethyl]tetrahydro-4-hydroxypyran-2-ones and/or oxides and the corresponding dihydroxy ring opened acids and esters useful as pharmaceutical agents, to methods for their production, to pharmaceutical compositions which include these compounds and a pharmaceutically acceptable carrier, and to pharmaceutical methods of treatment. More particularly, the novel compounds of the present invention are potent inhibitors of the enzyme 3-hydroxy-3-methylglutaryl-coenzyme A reductase (HMG-CoA reductase) and are thus useful as hypolipidemic and hypocholesterolemic agents.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine*, Volume 305, No. 9, pages 515–517 (1981)). It has now been established that lowering LDL-C levels affords protection from coronary heart disease (cf. *Journal of the American Medical Association*, Volume 251, No. 3, pages 351–374 (1984)).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer, et al, *Proceedings Society for Experimental Biology and Medicine*, Volume 102, pages 370–373 (1959) and F. H. Hulcher, *Archives of Biochemistry and Biophysics*, Volume 146, pages 422–427 (1971)).

U.S. Pat. Nos. 3,983,140; 4,049,495, and 4,137,322 disclose the fermentative production of a natural product, now called compactin, having an inhibitory effect on cholesterol biosynthesis. Compactin has been shown to have a complex structure which includes a mevalonolactone moiety (A. G. Brown, et al, *Journal of Chemical Society Perkin I*, pages 1165–1170 (1976)).

U.S. Pat. No. 4,761,419 discloses a series of 6-((substituted)quinolinyl)ethyl)-and ethenyl)tetrahydro-4-hydroxypyran-2-one inhibitors of cholesterol biosynthesis. We have found unexpectedly that incorporation of a 2-substituted amino group in the aforementioned series of compounds results in a series of novel inhibitors of 3-hydroxy-3-methylglutaryl-coenzyme A reductase which are useful hypolipidemic and hypocholesterolemic agents.

SUMMARY OF THE INVENTION

Accordingly, the present invention relates to novel compounds having the Formula I

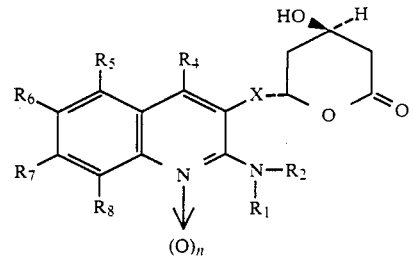

wherein X is —$CH_2$—$CH_2$— or —CH=CH—; $R_1$ and $R_2$ are independently hydrogen, alkyl of from one to four carbon atoms or $R_1$ and $R_2$ taken together form a ring of from three to six carbon atoms, which ring may be interrupted by a heteroatom comprising O, S or N—$R_3$, wherein $R_3$ is hydrogen or alkyl of from one to four carbon atoms; $R_4$ is
hydrogen,
alkyl of from one to six carbon atoms,
trifluoromethy,
cyclopropyl,
cyclohexyl,
cyclohexylmethyl,
phenyl,
    phenyl substituted with
    fluorine,
    chlorine,
    bromine,
    hydroxy,
    trifluoromethyl,
    alkyl of from one to four carbon atoms, or
    alkoxy of from one to four carbon atoms,
phenylmethyl,
phenylmethyl substituted with
    fluorine,
    chlorine
    bromine,
    hydroxy,
    trifluoromethyl,
    alkyl of from one to four carbon atoms, or
    alkoxy of from one to four carbon atoms,
2-pyrazinyl,
2-, 3-, or 4-pyridinyl or
2-, 4-, or 5-pyrimidinyl;
$R_5$, $R_6$, $R_7$, $R_8$ are independently selected from
hydrogen,
alkyl of from one to six carbon atoms,
trifluoromethyl,
cyclopropyl,
fluorine,
chlorine,
bromine,
hydroxy,
alkoxy of from one to four carbon atoms,
cyano,
nitro,
amino,
acetylamino,
aminomethyl,
phenyl,
phenyl substituted with
    fluorine,
    chlorine,
    bromine,
    hydroxy, trifluoromethyl,
alkyl of from one to four carbon atoms, or
alkoxy of from one to four carbon atoms,
phenylmethyl, or
phenylmethyl substituted with
   fluorine,
   chlorine,
   bromine,
   hydroxy,
   trifluoromethyl, or
   alkyl of from one to four carbon atoms;
n is 0 or 1;
or a corresponding 3,5-dihydroxy compound of Formula II

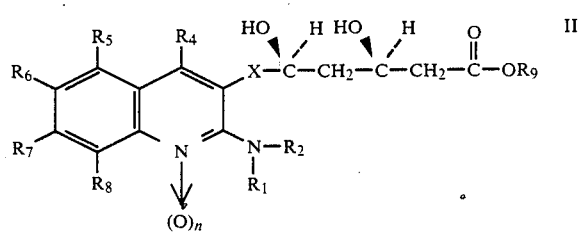

wherein $R_9$ is hydrogen or alkyl of from one to six carbon atoms and X, n, $R_1$, $R_2$, $R_4$, $R_5$, $R_6$, $R_7$, and $R_8$ are as defined above, or a pharmaceutically acceptable salt thereof.

Other embodiments of the present invention include pharmaceutical compositions comprising an effective amount of a compound of Formula I or Formula II in admixture with a pharmaceutically acceptable carrier, and a method of inhibiting cholesterol biosynthesis in a patient in need of said treatment comprising administering a cholesterol synthesis inhibiting amount of a compound of Formula I or Formula II in combination with a pharmaceutically acceptable carrier.

Finally, the present invention is directed to methods for production of compounds of Formula I and Formula II.

DETAILED DESCRIPTION OF THE INVENTION

Compounds of Formula I and Formula II comprise a class of trans-6-[2-[2-(substituted amino)-3-quinolinyl]ethenyl) and ethyl]tetrahydro-4-hydroxypyran-2-ones and/or oxides and the corresponding ring-opened hydroxy acids and esters derived therefrom in which the substituted quinoline nucleus is attached, through an ethenyl or ethyl group to the remainder of the molecule. When the bridging group between the substituted quinoline ring and the remainder of the molecule is ethyl, the configuration in the lactone ring is R*R*. Preferred compounds of the present invention are those in which the bridging group between the substituted quinoline ring and the remainder of the molecule is ethenyl, i.e., —CH=CH—, most preferably in the (E)-trans form and the configuration in the lactone ring is R*S*, the term "alkyl" means a straight or branched hydrocarbon radical having from one to six carbon atoms and includes, for example, methyl, ethyl, n-propyl, isopropyl, n-butyl, isobutyl, tertiary-butyl, n-pentyl, n-hexyl, and the like.

"Alkoxy" is O-alkyl in which alkyl is as defined above.

"Alkali metal" is a metal in Group IA of the periodic table and includes, for example, lithium, sodium, potassium and the like.

"Alkaline-earth metal" is a metal in Group IIA of the periodic table and includes, for example, calcium, barium, strontium and the like.

The compounds of Formula I are capable of further forming pharmaceutically acceptable acid addition salts. Both of these forms are within the scope of the present invention. Pharmaceutically acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al, "Pharmaceutical Salts", *Journal of Pharmaceutical Science,* 66, pp. 1–19 (1977)). The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

In the ring-opened dihydroxy acid form of Formula 11, compounds of the present invention may additionally form base salts. These forms are also within the scope of the present invention. Thus, base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge, S. M., et al, "Pharmaceutical Salts," *Journal of Pharmaceutical Science,* 66, pages 1–19 (1977)). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated as well as solvated forms, including hydrated forms. In general, the solvated forms, including hydrated forms are equivalent to unsolvated forms and are intended to be encompassed within the scope of the present invention.

The compounds of structural formula I possess two asymmetric carbon centers, one at the 4-hydroxy position of the pyran-2-one ring, and the other at the 6-position of the pyran-2-one ring where the ethenyl or ethylquinoline is attached. This asymmetry gives rise to four possible isomers, two of which are the R-cis and the S-cis isomers and the other two of which are the R-trans and S-trans isomers. This invention preferably contemplates the trans-form of the compounds of Formula I.

A preferred compound of Formula I or Formula II is one wherein $R_4$ is phenyl, or phenyl substituted with fluorine, chlorine, bromine, hydroxy, trifluoromethyl, alkyl of from one to four carbon atoms, or alkoxy of from one to four carbon atoms.

Another preferred embodiment is a compound of Formula I or Formula II wherein $R_1$ and $R_2$ are independently alkyl of from one to four carbon atoms or $R_1$ and $R_2$ taken together form a ring of from three to six carbon atoms which ring may be interrupted by a heteroatom comprising O, S, or N-$R_3$, wherein $R_3$ is hydrogen or alkyl of from one to four carbon atoms.

Particularly valuable are:

[4α,6β(E)]-6-[2-[2-(dimethylamino)-4-(4-fluorophenyl)-3-quinolinyl]ethenyl]tetrahydro-4-hydroxy-2H-pyran-2-one;

[4α,6β(E)]-6-[2-[2-(ethylmethylamino)-4-(4-fuorophenyl)-3-quinolinyl]ethenyl]tetrahydro-4-hydroxy-2H-pyran-2-one;

[4α,6β(E)]-6-[2-[2-(diethylamino)-4-(4-fluorophenyl)-3-quinolinyl]ethenyl]tetrahydro-4-hydroxy-2H-pyran-2-one;

4α,6β(E)]-6-[2-4-(4-fluorophenyl)-2-(1-pyrrolidinyl)-3-quinolinyl]ethenyl]tetrahydro-4-hydroxy-2H-pyran-2-one;

[4α,6β(E)]-6[2-4-(4-fluorophenyl)-2-(1-piperidinyl)-3-quinolinyl]ethenyl]tetrahydro-4-hydroxy-2H-pyran-2-one;

[4α,6β(E)]-6-[2-4-(4-fluorophenyl)-2-(4-morpholinyl)-3-quinolinyl]ethenyl]tetrahydro-4-hydroxy-2H-pyran-2-one;

[4α,6β(E)]-6-[2-[4-(4-fluorophenyl)-2-(4-thiomorpholinyl)-3-quinolinyl]ethenyl]tetrahydro-4-hydroxy-2H-pyran-2-one;

[4α,6β(E)]-6-[2-[4-(4-fluorophenyl)-2-(1-piperazinyl-3-quinolinyl]ethenyl]tetrahydro-4-hydroxy-2H-pyran-2-one;

4α,6β(E)]-6-[2-[4-(4-fluorophenyl)-2-(4-methyl-1-piperazinyl)-3-quinolinyl]ethenyl]tetrahydro-4-hydroxy-2H-pyran-2-one;

[4α,6α]-6-[2-[2-(dimethylamino)-4-(4-fluorophenyl)-3-quinolinyl]ethyl]tetrahydro-4-hydroxy-2H-pyran-2-one;

4α,6α]-6-[2-[2-(ethylmethylamino)-4-(4-fluorophenyl)-3-quinolinyl]ethyl]tetrahydro-4-hydroxy-2H-pyran-2-one;

[4α,6α]-6-[2-2-(diethylamino)-4-(4-fluorophenyl)-3-quinolinyl]ethyl]tetrahydro-4-hydroxy-2H-pyran-2-one;

[4α,6α]-6-[2-[4-(4-fluorophenyl)-2-(1-pyrrolidinyl)-3-quinolinyl]ethyl]tetrahydro-4-hydroxy-2H-pyran-2-one;

[4α,6α]-6-[2-[4-(4-fluorophenyl)-2-(1-piperidinyl)-3-quinolinyl]ethyl]tetrahydro-4-hydroxy-2H-pyran-2-one;

[4α,6α]-6-[2-[4-(4-fluorophenyl)-2-(4-morpholinyl)-3-quinolinyl]ethyl]tetrahydro-4-hydroxy-2H-pyran-2-one;

[4α,6α]-6-[2-[4-(4-fluorophenyl)-2-(4-thiomorpholinyl)-3-quinolinyl]ethyl]tetrahydro-4-hydroxy-2H-pyran-2-one;

4α,6α]-6-[2-[4-(4-fluorophenyl)-2-(1-piperazinyl)-3-quinolinyl]ethyl]tetrahydro-4-hydroxy-2H-pyran-2-one;

and [4α,6α]-6-[2-[4-(4-fluorophenyl)-2-(4-methyl-1-piperazinyl)-3-quinolinyl]ethyl]tetrahydro-4-hydroxy-2H-pyran-2-one;

or a pharmaceutically acceptable salt thereof.

The compounds of this invention are useful as hypocholesterolemic or hypolipidemic agents by virtue of their ability to inhibit the biosynthesis of cholesterol through inhibition of the enzyme 3-hydroxy-3-methyl-glutaryl-coenzyme A reductase (HMG-CoA reductase).

The ability of compounds of the present invention to inhibit the biosynthesis of cholesterol was measured by a method (designated CSI (Cholesterol Synthesis Inhibition) screen) which utilizes the procedure described by R. E. Dugan et al, *Archives of Biochemistry and Biophysics*, Volume 152, pages 21–27 (1972). In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of $^{14}$C-acetate into nonsaponifiable lipid by the rat liver homogenate is measured. The micromolar concentration of compound required for 50% inhibition of sterol synthesis over a one-hour period is measured, and expressed as an IC$_{50}$ value.

Additionally, the ability of compounds of the present invention to inhibit the biosynthesis of cholesterol was also measured by a method (designated AICS (Acute Inhibition of Cholesterol Synthesis) screen) which utilizes the procedure described by A. W. Alberts, et al, *Proceedings of the National Academy of Sciences*, Volume 77, pages 3957–3961 (1980).

In this method male Sprague-Dawley rats (200 g body weight) previously fed 5% cholestyramine for three days were randomly divided into groups (N=5/group) and given a single dose of vehicle (controls) or compound by an oral gavage at the indicated doses. One hour after drug dosing, all rats were injected intraperitoneally with sodium[1-$^{14}$C]acetate (18.75 μCi/rat in 0.2 ml saline). After 50 minutes, blood samples were taken, plasma obtained by centrifugation, and plasma [$^{14}$C]cholesterol measured after saponification and extraction.

The data in the Table shows the activity of representative compounds of the present invention:

TABLE

| | Biological Activity of Compounds of Formula I and Formula II | | |
|---|---|---|---|
| Example Number | Compound | CSI IC$_{50}$ μMole/Liter | AICS % Inhibition |
| 1 (3,5-dihydroxy acid monosodium salt form) | [R*,S*-(E)]-7-[2-(Dimethylamino)-4-(4-fluorophenyl)-3-quinolinyl]-3,5-dihydroxy-6-heptenoic acid | 0.047 | 49 |
| 1 (lactone) | [4α,6β(E)]-6-[2-[2-(Dimethylamino)-4-(4-fluorophenyl)-3-quinolinyl]ethenyl]tetrahydro-4-hydroxy-2H-pyran-2-one | | 52 |

The process of preparing compounds of the present invention is outlined in the following scheme:

SCHEME I
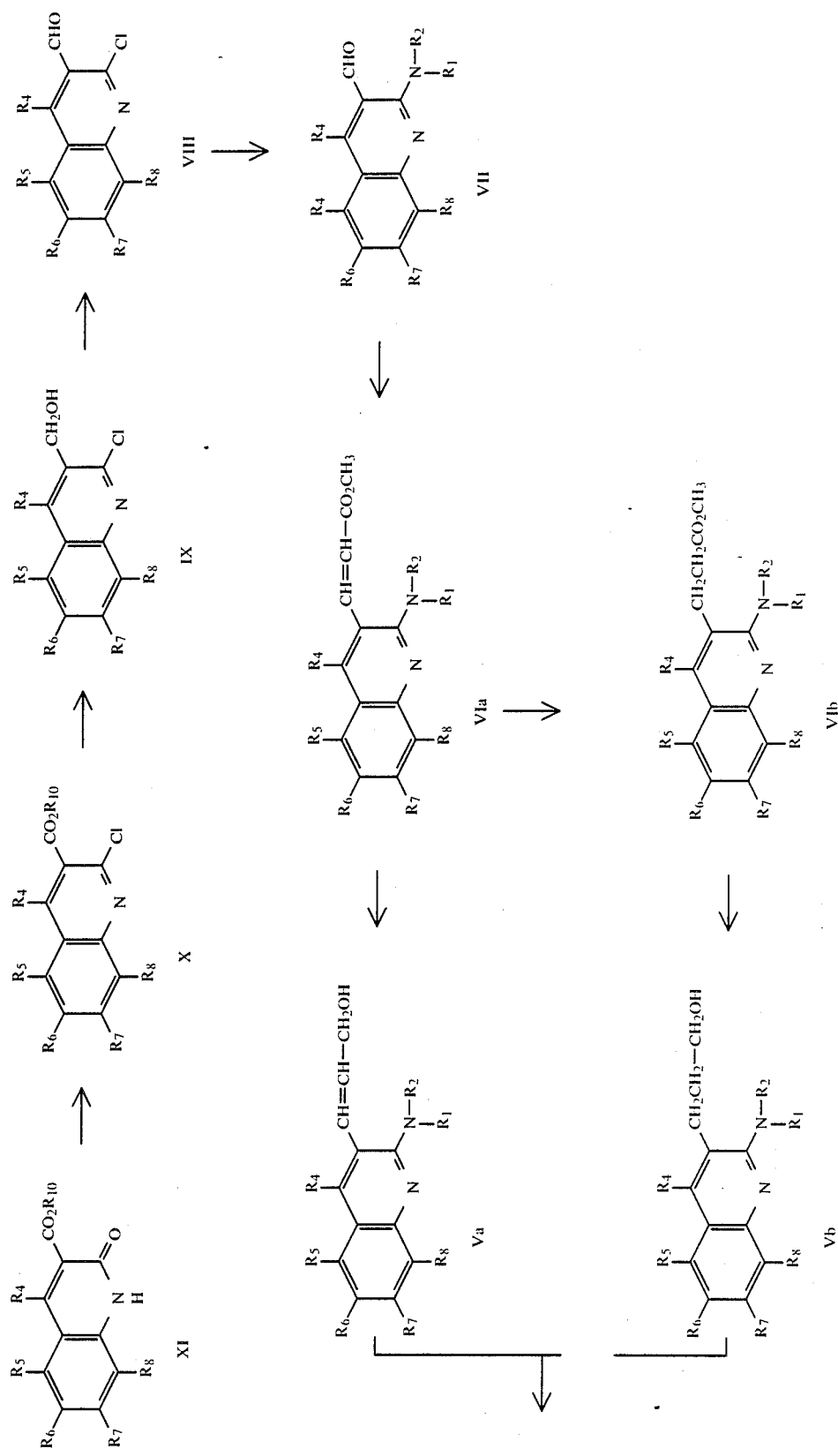

-continued
SCHEME I
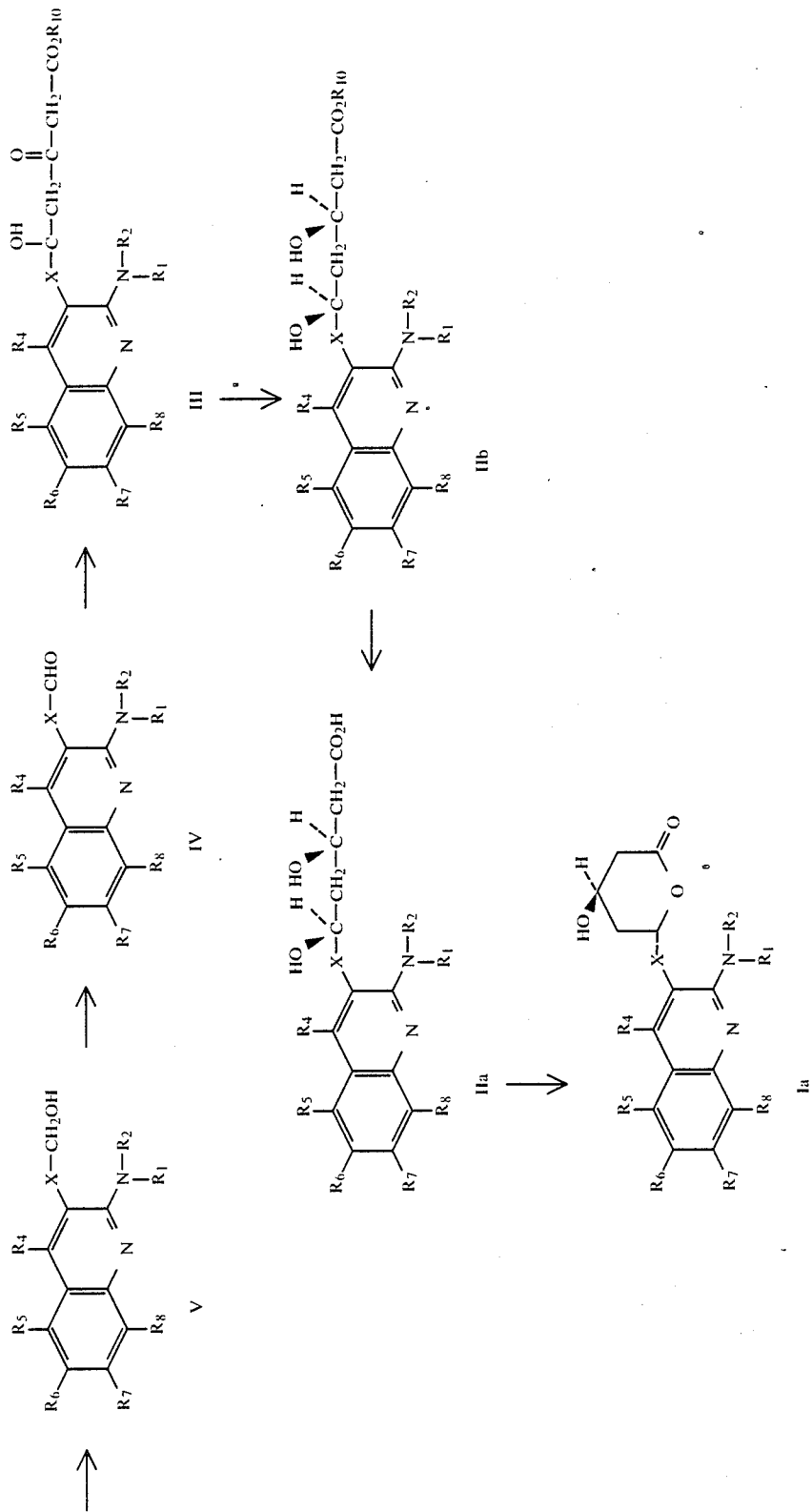

A compound of Formula XI is prepared by reacting a compound of Formula XII

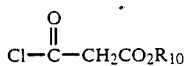   XII wherein $R_{10}$ is alkyl of from one to six carbon atoms with a compound of Formula XIII

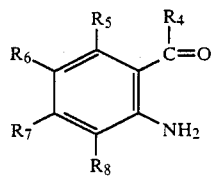   XIII wherein $R_4$ is
hydrogen,
alkyl of from one to six carbon atoms,
trifluoromethyl,
cyclopropyl,
cyclohexyl,
cyclohexylmethyl,
phenyl,
phenyl substituted with
    fluorine,
    chlorine,
    bromine,
    hydroxy,
    trifluoromethyl,
    alkyl of from one to four carbon atoms, or
    alkoxy of from one to four carbon atoms,
phenylmethyl,
phenylmethyl substituted with
    fluorine,
    chlorine,
    bromine,
    hydroxy,
    trifluoromethyl,
    alkyl of from one to four carbon atoms, or
    alkoxy of from one to four carbon atoms,
2-pyrazinyl,
2-, 3-, or 4-pyridinyl, or
2-, 4-, or 5-pyrimidinyl;
$R_5$, $R_6$, $R_7$, $R_8$ are independently selected from
hydrogen,
alkyl of from one to six carbon atoms,
trifluoromethyl,
cyclopropyl,
fluorine,
chlorine,
bromine,
hydroxy,
alkoxy of from one to four carbon atoms,
cyano,
nitro,
amino,
acetylamino,
aminomethyl,
phenyl,
phenyl substituted with
    fluorine,
    chlorine,
    bromine,
    hydroxy,
    trifluoromethyl,
    alkyl of from one to four carbon atoms, or
    alkoxy of from one to four carbon atoms,
phenylmethyl, or
phenylmethyl substituted with
    fluorine,
    chlorine,
    bromine,
    hydroxy,
    trifluoromethyl, or
    alkyl of from one to four carbon atoms;
in a solvent such as, for example, dichloromethane and the like at about 0° C. to give an intermediate which is not isolated but treated in situ with a dehydrating agent such as, for example, silica gel and the like to give a compound of Formula XI, wherein $R_4$, $R_5$, $R_6$, $R_7$, $R_8$, and $R_{10}$ are as defined above. A compound of Formula XI is treated with phosphorus oxychloride at about the reflux temperature of phosphorus oxychloride to give a compound of Formula X, wherein $R_4$, $R_5$, $R_6$, $R_7$, $R_8$, and $R_{10}$ are as defined above. A compound of Formula X is treated with a reducing agent such as, for example, diisobutylaluminum hydride (DIBAL) and the like in a solvent such as, for example, dichloromethane and the like at about $-78°$ C. to give a compound of Formula IX, wherein $R_4$, $R_5$, $R_6$, $R_7$, and $R_8$ are as defined above. A compound of Formula IX is treated with an oxidizinq agent such as, for example, manganese dioxide in a solvent such as, for example, toluene and the like at about the reflux temperature of the solvent or, alternatively, oxidation is carried out by the method of Swern (Swern et al, *Journal of Organic Chemistry*, Volume 43, pages 2480-2482 (1978)) to give a compound of Formula VIII, wherein $R_4$, $R_5$, $R_6$, $R_7$, and $R_8$ are as defined above. A compound of Formula VIII is treated with a compound of Formula XIV

   XIV wherein $R_1$ and $R_2$ are independently hydrogen, alkyl of from one to four carbon atoms or $R_1$ and $R_2$ taken together form a ring of from three to six carbon atoms which ring may be interrupted by a heteroatom comprising O, S, or N—$R_3$, wherein $R_3$ is hydrogen or alkyl Of from one to four carbon atoms in an inert solvent such as, for example, toluene and the like in an autoclave for about 14 hours at about 123°-136° C. to give a compound of Formula VII, wherein $R_1$, $R_2$, $R_4$, $R_5$, $R_6$, $R_7$, and $R_8$ are as defined above. A compound of Formula VII is dissolved in an inert solvent such as, for example, dichloromethane and the like and treated with an yield such as, for example, methyl (triphenylphosphoranylidene) acetate at about room temperature for about three days to give a compound of Formula VIa, wherein $R_1$, $R_2$, $R_4$, $R_5$, $R_6$, $R_7$, and $R_8$ are as defined above. An unsaturated ester of Formula VIa is dissolved in an inert solvent such as, for example, dichloromethane and the like and treated with 2 equivalents of diisobutylaluminum hydride (DIBAL) at about $-78°$ C. to give an unsaturated alcohol of Formula Va, wherein $R_1$, $R_2$, $R_4$, $R_5$, $R_6$, $R_7$, and $R_8$ are as defined above. Alternatively, an unsaturated ester of Formula VIa is reduced by the action of hydrogen in the presence of a catalyst such as, for example, palladium on charcoal to give a saturated ester of Formula VIb, wherein $R_1$, $R_2$, $R_4$, $R_5$, $R_6$, $R_7$, and $R_8$ are as defined above. A saturated ester of Formula VIb is converted to a saturated alcohol of Formula Vb, wherein $R_1$, $R_2$, $R_4$, $R_5$, $R_6$, $R_7$, and $R_8$ are as defined above by following the same procedure used to prepare a compound of Formula Va.

An unsaturated alcohol of Formula Va and a saturated alcohol of Formula Vb represented by general Formula V, wherein X represents $-CH_2CH_2-$ or $-CH=CH-$ and $R_1$, $R_2$, $R_4$, $R_5$, $R_6$, $R_7$, and $R_8$ are as defined above undergo the following similar transformations. Thus, a compound of Formula V is treated with an oxidizing agent such as, for example, manganese dioxide or alternatively oxidation is carried out by the method of Swern (Swern, et al, *Journal of Organic Chemistry*, Volume 43, pages 2480–2482 (1978)) to give a compound of Formula IV, wherein X, $R_1$, $R_2$, $R_4$, $R_5$, $R_6$ $R_7$, and $R_8$ are as defined above. Aldol condensation of a compound of Formula IV with the sodium lithium dianion of a compound of Formula XV

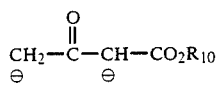

wherein $R_{10}$ is as defined above, in a solvent such as, for example, tetrahydrofuran and the like at about $-78°$ C. gives a compound of Formula III, wherein $R_1$, $R_2$, $R_4$, $R_5$, $R_6$, $R_7$, $R_8$, and $R_{10}$ are as defined above. A compound of Formula III is then reduced in a sequence of steps in which it is first dissolved in a solvent such as, for example, tetrahydrofuran and the like under a dry atmosphere. A small excess of a trialkylborane such as, for example, triethylborane and catalytic amounts of 2,2-dimethylpropanoic acid are next added. The mixture is stirred at about room temperature for a short period, after which it is cooled to a temperature between about $-60°$ and $-80°$ C., preferably about $-78°$ C. Dry methanol is added, followed by sodium borohydride. The mixture is kept at low temperature for about four to eight hours, preferably for about six hours at about $-78°$ C., before treating it with aqueous hydrogen peroxide solution to give a compound of Formula IIb, wherein $R_1$, $R_2$, $R_4$, $R_5$, $R_6$, $R_7$, $R_8$, and $R_{10}$ are as defined above. A compound of Formula IIb may be utilized as such in the pharmaceutical method of this invention, or may be converted, if desired, to the corresponding acid salt form, such as, for example, the sodium salt, employing basic hydrolysis by conventional well-known methods. A free acid of Formula IIa, wherein $R_1$, $R_2$, $R_4$, $R_5$, $R_6$, $R_7$, and $R_8$, produced by acidification, for example, of the sodium salt, can be dehydrated to a laotone of Formula I, wherein $R_1$, $R_2$, $R_4$, $R_5$, $R_6$, $R_7$, and $R_8$ are as defined above, by heating the acid in an inert solvent such as, for example, toluene and the like with concomitant azeotropic removal of water.

Further, a compound of Formula Ib

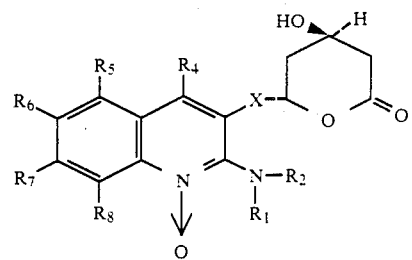

wherein X, $R_1$, $R_2$, $R_4$, $R_5$, $R_6$, $R_7$, and $R_8$ are as defined above is prepared from a compound of Formula Ia

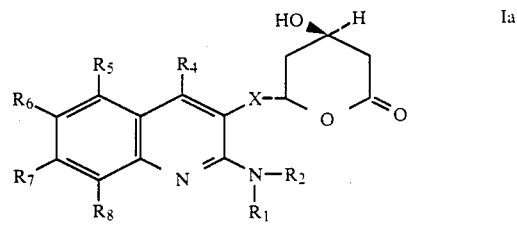

wherein X, $R_1$, $R_2$, $R_4$, $R_5$, $R_6$, $R_7$, and $R_8$ are as defined above by mild oxidation methods known in the art using, for example, peracetic acid, perbenzoic acid, hydrogen peroxide and the like in the presence of a solvent.

Additionally, a compound of Formula IId

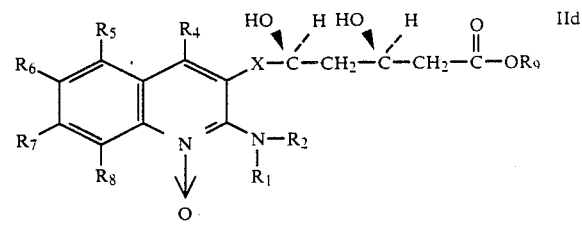

wherein $R_9$ is hydrogen or alkyl of from one to six carbon atoms and X, $R_1$, $R_2$, $R_4$, $R_5$, $R_6$, $R_7$, and $R_8$ are as defined above is prepared from a compound of Formula IIc

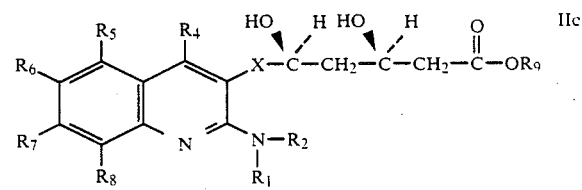

wherein X, $R_1$, $R_2$, $R_4$, $R_5$, $R_6$, $R_7$, $R_8$ and $R_9$ are as defined above using the methodology described for preparing a compound of Formula Ib from a compound of Formula Ia.

Compounds of Formula XII, Formula XIII, Formula XIV, or Formula XV are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or, Formula II or a corresponding pharmaceutically acceptable salt of a compound of Formula I or Formula II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 20 mg to 600 mg per day. The composition can, if desired, also contain other compatible therapeutic agents.

In therapeutic use as hypolipidemic or hypocholesterolemic agents, the compounds utilized in the pharmaceutical method of this invention are administered at the initial dosage of about 0.5 mg to about 8.0 mg per kilogram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

$4\alpha,6\beta(E)$)]-6-[2-[2-(Dimethylamino)-4-(4-fluorophenyl)-3-quinolinyl]ethenyl]tetrahydro-4-hydroxy-$2\underline{H}$-pyran-2-one

STEP A: Preparation of Ethyl 4-(4-fluorophenyl)-1,2-dihydro-2-oxo-3-quinolinecarboxylate Ethyl malonyl chloride (125 g, 1.2 equivalents) is added in portions to a solution of 150 g of (2-aminophenyl)-4-(fluorophenyl)methanone (R. Combs, et al, *Journal of Medicinal Chemistry*, Volume 16, pages 1237–1245 (1973)) in 1 L of dichloromethane at 0° C. under an atmosphere of nitrogen. The reaction is slowly warmed to room temperature over one hour, washed with saturated aqueous potassium carbonate solution, dried (magnesium sulfate), and concentrated to ~600 ml. Silica, 50 g, is then suspended in the organic solution, and stirred overnight. The mixture is filtered and the silica is washed with ethyl acetate. The filtrate is evaporated and the residue triturated with hexanes to give 192 g (88%) of ethyl 4-(4-fluorophenyl)-1,2-dihydro-2-oxo-3-quinolinecarboxylate as a white solid; mp 204°–206° C.; $^1$H NMR (nuclear magnetic resonance) (chloroform-d): δ 12.60 (bs, 1H), 7.60–7.10 (m, 8H), 4.17 (q, 2H), 1.04 (t, 3H) ppm.

STEP B: Preparation of Ethyl 2-Chloro-4-(4-fluorophenyl)-3-quinolinecarboxylate Ethyl 4-(4-fluorophenyl)-1,2-dihydro-2-oxo-3-quinolinecarboxylate (12.8 g) is dissolved in 40 ml of phosphorus oxychloride under an atmosphere of nitrogen. The resulting solution is refluxed one hour, cooled, concentrated, and the residue neutralized with cold 1N sodium hydroxide solution and extracted with ethyl acetate. The organic extracts are filtered through a bed of silica to give 13.2 g of ethyl 2-chloro-4-(4-fluorophenyl)-3-quinolinecarboxylate as a white solid; mp 113°–114° C.; $^1$H NMR (chloroform-d): δ 8.02 (d, 1H), 7.75–7.70 (m, 1H), 7.52–7.43 (m, 2H), 7.34–7.28 (m, 2H), 7.20–7.12 (m, H), 4.14–4.07 (q, 2H), 1.02 (t, 3H) ppm.

STEP C: Preparation of 2-Chloro-4-(4-fluorophenyl)-3-quinolinemethanol

Ethyl 2-chloro-4-(4-fluorophenyl)-3-quinolinecarboxylate (12.91 g) is dissolved in 200 ml of dichloromethane at −78° C. under an atmosphere of nitrogen. A solution of diisobutylaluminum hydride (DIBAL) (97 ml, 2.5 equivalents) in dichloromethane is added dropwise and the reaction stirred for 3.5 hours at −78° C. The reaction is quenched by addition of a saturated solution of sodium sulfate (20 ml) and removing the cooling bath. The gelatinous mass is filtered through Celite, washed with hot ethyl acetate, and the filtrate evaporated to give 9.36 g of 2-chloro-4-(4-fluorophenyl)-3-quinolinemethanol as a white solid; mp 159°–160° C.; $^1$H NMR (chloroform-d): δ 8.07 (d, 1H), 7.79–7.70 (m, 1H), 7.53–7.22 (m, 6H), 4.67 (d, 2H), 2.24 (t, 1H) ppm.

STEP D: Preparation of 2-Chloro-4-(4-fluorophenyl)-3-quinolinecarboxaldehyde To a solution of oxalyl chloride (2.88 ml, 1.3 equivalents), in 25 ml of dichloromethane at −78° C. under nitrogen is added dropwise a solution of dimethylsulfoxide (DMSO) (4.70 ml, 2.6 equivalents) in 25 ml of dichloromethane. After addition, the mixture is stirred for 15 minutes at −78° C. and then a solution of 2-chloro-4-(4-fluorophenyl)-3-quinolinemethanol (7.30 g) in 50 ml dichloromethane and 20 ml dimethyl sulfoxide is added dropwise. The resulting mixture is stirred at −78° C. for one hour and then quenched by adding triethylamine (17.7 ml, 5.0 equivalents), and removing the cooling bath. A saturated aqueous solution of ammonium chloride is added. The organic layer is separated, washed with water, dried (magnesium sulfate), and evaporated to give 6.56 g of 2-chloro-4-(4-fluorophenyl)-3-quinolinecarboxaldehyde as a yellow solid; mp 168°–169.5° C.; $^1$H NMR (chloroform-d): δ 10.25 (s, 1H), 8.12 (d, 1H), 7.91–7.83 (m, 1H), 7.57–7.53 (m, 2H), 7.36–7.22 (m, 4H) ppm.

STEP E: Preparation of 2-(Dimethylamino)-4-(4-fluorophenyl)-3-quinolinecarboxaldehyde 2-Chloro-4-(4-fluorophenyl)-3-quinolinecarboxaldehyde (5.28 g) and 15 ml of dimethylamine are dissolved in 75 ml of toluene. This mixture is autoclaved for 14 hours at 123°–136° C. The mixture is cooled, evaporated to dryness, and partitioned between ethyl acetate and a saturated aqueous solution of potassium carbonate. The ethyl acetate layer is dried (magnesium sulfate) and evaporated to give an orange oil. Chromatography (silica, 10% ethyl acetate/hexanes) gives 4.20 g of 2-(dimethylamino)-4-(4-fluorophenyl)-3-quinolinecarboxaldehyde as an orange solid; $^1$H NMR (chloroform-d): δ 9.73 (s, 1H), 7.78–6.96 (m, 8H), 3.10 (s, 6H) ppm.

STEP F: Preparation of (E)-Methyl 3-[2-(dimethylamino)-4-(4-fluorophenyl)-3-quinolinyl]-2-propenoate 2-(Dimethylamino)-4-(4-fluorophenyl)-3-quinolinecarboxaldehyde (4.20 g) is dissolved in 100 ml of dichloromethane and (5.25 g, 1.1 equivalents) of methyl (triphenylphosphoranylidene) acetate is added in one portion. The reaction is stirred at room temperature for three days, evaporated, and the residue eluted through a 3-inch silica column to give 4.60 g of (E)-methyl-3-[2-(dimethylamino)-4-(4-fluorophenyl)-3-quinolinyl]-2-propenoate as an orange solid; $^1$H NMR (chloroform-d): δ 7.78–6.87 (m, 9H), 5.98 (d, 1H), 3.60 (s, 3H), 2.95 (s, 6H) ppm.

STEP G: Preparation of (E)-3-[2-(Dimethylamino)-4-(4-fluorophenyl)-3-quinolinyl]-2-propen-1-ol (E)-Methyl-3-[2-(dimethylamino)-4-(4-fluorophenyl)-3-quinolinyl]-2-propenoate (4.60 g) is dissolved in 40 ml of dichloromethane at −78° C. under an atmosphere of nitrogen. A 1 M solution of diisobutylaluminum hydride (DIBAL) (29 ml, 2.2 equivalents), in dichloromethane is added dropwise, the reaction stirred for one hour, and quenched by adding 15 ml of an aqueous saturated solution of sodium sulfate and removing the cooling bath. The reaction mixture is filtered through Celite and the filtrate dried (magnesium sulfate) and evaporated to give 4.61 g of (E)-3-[2-(dimethylamino)-4-(4-fluorophenyl)-3-quinolinyl]-2-propen-1-ol as an orange oil; $^1$H NMR (chloroform-d): δ 7.72 (d, 1H), 7.50–7.30 (m, 1H), 7.20–6.98 (m, 6H), 6.31 (d, 1H), 5.72 (dt, 1H), 3.99 (bd, 2H), 2.96 (s, 6H), 1.54 (bs, 1H) ppm.

STEP H: Preparation of (E)-3-[2-(Dimethylamino)-4-(4-fluorophenyl)-3-quinolinyl]-2-propenal To a solution of oxalyl chloride (1.21 ml, 1.3 equivalents), in 40 ml of dichloromethane at −78° C. under an atmosphere of nitrogen, is added a solution of 2.0 ml (2.6 equivalents) of dimethylsulfoxide in 25 ml of dichloromethane. The reaction is stirred at −78° C. for 15 minutes and 3.45 g of (E)-3-[2-(dimethylamino)-4-(4-fluorophenyl)-3-quinolinyl]-2-propen-1-ol in 40 ml of dichloromethane added dropwise. The reaction is stirred for one hour at −78° C. and then quenched by adding 7.46 ml (5.0 equivalents) of triethylamine and warming to room temperature. A saturated aqueous solution of ammonium chloride, 20 ml, is added and the reaction is washed with water, dried (magnesium sulfate), and evaporated to give 3.14 g of (E)-3-[2-(dimethylamino)-4-(4-fluorophenyl)-3-quinolinyl]-2-propenal as an orange solid; $^1$H NMR (chloroform-d): δ 9.35 (d, 1H), 7.75 (d, 1H), 7.58–6.98 (m, 8H), 6.32 (dd, 1H), 2.99 (s, 6H) ppm.

STEP I: Preparation of (E)-Ethyl 7-[2-(dimethylamino)-4-(4-fluorophenyl)-3-quinolinyl]-5-hydroxy-3-oxo-6-heptenoate To a hexane washed suspension of 0.73 g of sodium hydride (1.6 equivalents) in 20 ml of tetrahydrofuran at 0° C. under an atmosphere of nitrogen is added dropwise a solution of ethyl acetoacetate (2.16 ml, 1.5 equivalents) in 20 ml of tetrahydrofuran. The resulting clear solution is stirred at 0° C. for 15 minutes and then n-butyllithium (6.8 ml, 1.5 equivalents) is added dropwise. The resulting orange solution is stirred at 0° C. for 15 minutes, cooled to −78° C., and 3.62 g of (E)-3-2-(dimethylamino)-4-(4-fluorophenyl)-3-quinolinyl]-2-propenal in 60 ml of tetrahydrofuran is added dropwise. One hour after addition, the reaction is quenched by addition of 3 ml glacial acetic acid and removing the cooling bath. The reaction mixture is partitioned between diethyl ether and a 5% aqueous solution of potassium carbonate. The diethyl ether layer is separated, washed with a 5% aqueous solution of potassium carbonate, water, and dried (magnesium sulfate). Removal of the solvent gives 5.5 g of an orange oil. Column chromatography (silica gel; 40% ethyl acetate/hexane) gives 3.96 g of (E)-ethyl 7-[2-(dimethylamino)-4-(4-fluorophenyl)-3-quinolinyl]-5-hydroxy-3-oxo-6-heptenoate as a yellow oil; $^1$H NMR (chloroform-d): δ 7.75 (d, 1H), 7.53–7.34 (m, 1H), 7.20–7.00 (m, 6H), 6.39 (d, 1H), 5.56 (dd, 1H), 4.57–4.36 (m, 1H), 4.12 (q, 2H), 3.37 (s, 2H), 2.96 (s, 6H), 2.50 (d, 2H), 1.24 (t, 3H) ppm.

STEP J: Preparation of [R*,S*-(E)]-Ethyl 7-2-(dimethylamino)-4-[4-fluorophenyl]-3-quinolinyl]-3-5-dihydroxy-6-heptenoate Triethylborane (8.6 ml, 1.1 equivalents), is added in one portion to 3.51 g of (E)-ethyl 7-2-dimethylamino)-4-(4-fuorophenyl]-3-quinolinyl]-5-hydroxy-3-oxo-6-heptenoate and 2,2-dimethylpropanoic acid (0.88 g, 0.1 equivalents), in 50 ml of tetrahydrofuran under a dry air atmosphere. The resulting orange solution is stirred for 15 minutes at room temperature, cooled to −78° C., and 10 ml of methanol and sodium borohydride (0.29 g, 1.1 equivalents) is added. The resulting effervescent solution is stirred at −78° C. for six hours and quenched by pouring into 5 ml of cold 30% hydrogen peroxide solution and stirring overnight. The reaction is partitioned between chloroform and water, the organic layer separated, washed extensively with water, dried (magnesium sulfate), and evaporated to give 3.54 g of [R*,S*-(E)]-ethyl 7-[2-(dimethylamino)-4-(4-fluorophenyl)-3-quinolinyl]-3,5-dihydroxy-6-heptenoate as a yellow foam which is used in the next step without further purification.

STEP K: Preparation of [R*,S*-(E)-]-7-[2-(Dimethylamino)-4-(4-fluorophenyl)-3-quinolinyl]-3,5-dihydroxy-6-heptenoic acid Sodium hydroxide (6.5 ml, 1.2 equivalents of 1N solution), is added to a solution of 2.44 g of [R*,S*-(E)]-ethyl 7-[2-(dimethylamino)-4-(4-fluorophenyl)-3-quinolinyl]-3,5-dihydroxy-6-heptenoate in 100 ml of tetrahydrofuran and 5 ml of methanol. The reaction is stirred overnight at room temperature and evaporated to dryness to give [R*,S*-(E)]-7-[2-dimethylamino)-4-(4-fluorophenyl)-3-quinolinyl]-3,5-dihydroxy-6-heptenoic acid, monosodium salt (mp 205°–215° C.). The aforementioned sodium salt is dissolved in 25 ml of water and washed with diethyl ether. The aqueous solution is separated, neutralized with 4.9 ml of 1N hydrochloric acid solution, and extracted with ethyl acetate. The organic extract is dried (magnesium sulfate) and evaporated to give 1.66 g of [R*,S*-(E)]-7-2-(dimethylamino)-4-(4-fluorophenyl)-3-quinolinyl]-3,5-dihydroxy-6-heptenoic acid as a yellow foam.

STEP L: Preparation of [4α,6β(E)]-6-[2-[2-(Dimethylamino)-4-(4-fluorophenyl)-3-quinolinyl]ethenyl]tetrahydro-4-hydroxy-2H-pyran-2-one

[R*,S*-(E)-]-7-[2-(Dimethylamino)-4-(4-fluorophenyl)-3-quinolinyl]-3,5-dihydroxy-6-heptenoic acid (1.66 g) is dissolved in 150 ml of toluene and heated at reflux for 20 hours with the azeotropic removal of water. Cooling and concentration gives a yellow oil. Column chromatography (silica gel, 50% ethyl acetate/hexane) gives 0.8 g of [4α,6β(E)]-6-[2-[2-(dimethylamino)-4-(4-fluorophenyl-3-quinolinyl]ethenyl]tetrahydro-4-hydroxy-2H-pyran-2-one as an off-white solid; mp 150°–152° C.; $^1$H NMR (chloroform-d): δ 7.83 (d, 1H), 7.57–7.50 (m, 1H), 7.26–7.16 (m, 6H), 6.49 (d, 1H), 5.66 (dd, 1H), 5.16–5.06 (m, 1H), 4.28–4.25 (m, 1H), 3.01 (s, 6H), 2.75–2.60 (ABq, 2H), 2.07 (bs, 1H), 1.82–1.51 (m, 1H) ppm.

We claim:

1. A compound of Formula I

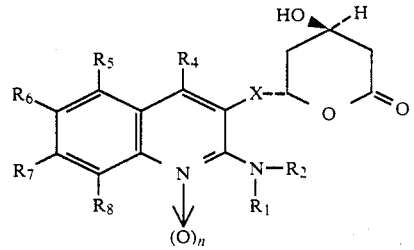

wherein X is —CH$_2$CH$_2$— or —CH=CH—; R$_1$ and R$_2$ are independently hydrogen, alkyl of from one to four carbon atoms or R$_1$ and R$_2$ taken together form a ring of from three to six carbon atoms, which ring may be interrupted by a heteroatom comprising O, S or N—R$_3$, wherein R$_3$ is hydrogen or alkyl of from one to four carbon atoms; R$_4$ is
  hydrogen,
  alkyl of from one to six carbon atoms,
  trifluoromethyl,
  cyclopropyl,
  cyclohexyl,
  cyclohexylmethyl,
  phenyl,
  phenyl substituted with
    fluorine,
    chlorine,
    bromine,
    hydroxy,
    trifluoromethyl,
    alkyl of from one to four carbon atoms, or
    alkoxy of from one to four carbon atoms,
  phenylmethyl,
  phenylmethyl substituted with
    fluorine,
    chlorine,
    bromine,
    hydroxy,
    trifluoromethyl,
    alkyl of from one to four carbon atoms, or
    alkoxy of from one to four carbon atoms,
  2-pyrazinyl,
  2-, 3-, or 4-pyridinyl, or
  2-, 4-, or 5-pyrimidinyl;
R$_5$, R$_6$, R$_7$, R$_8$ are independently selected from hydrogen,
  alkyl of from one to six carbon atoms,
  trifluoromethyl,
  cyclopropyl,
  fluorine,
  chlorine,
  bromine,
  hydroxy,
  alkoxy of from one to four carbon atoms,
  cyano,
  nitro,
  amino,
  acetylamino,
  aminomethyl,
  phenyl, phenyl substituted with
fluorine,
chlorine,
bromine,
hydroxy,
trifluoromethyl,
alkyl of from one to four carbon atoms, or
alkoxy of from one to four carbon atoms,
phenylmethyl, or
phenylmethyl substituted with
fluorine,
chlorine,
bromine,
hydroxy,
trifluoromethyl, or
alkyl of from one to four carbon atoms;
n is 0 or 1;
or a corresponding 3,5-dihydroxy compound of Formula II

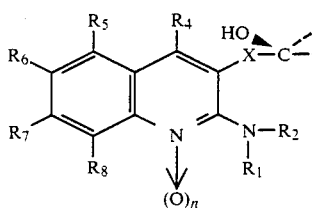

wherein $R_9$ is hydrogen or alkyl of from one to six carbon atoms and X, n, $R_1$, $R_2$, $R_4$, $R_5$, $R_6$, $R_7$, $R_8$ and n are as defined above, or a pharmaceutically acceptable salt thereof.

2. A compound as defined in claim 1 wherein $R_4$ is phenyl, or phenyl substituted with fluorine, chlorine, bromine, hydroxy, trifluoromethyl, alkyl of from one to four carbon atoms, or alkoxy of from one to four carbon atoms.

3. A compound as defined in claim 2 wherein $R_1$ and $R_2$ are independently alkyl of from one to four carbon atoms or $R_1$ and $R_2$ taken together form a ring of from three to six carbon atoms which ring may be interrupted by a heteroatom comprising O, S or N—$R_3$, wherein $R_3$ is hydrogen or alkyl of from one to four carbon atoms.

4. A compound as defined in claim 3 selected from the group consisting of
[4α,6β(E)]-6-[2-[2-(dimethylamino)-4-(4-fluorophenyl)-3-quinolinyl]ethenyl]tetrahydro-4-hydroxy-2H-pyran-2-one;
[4α,6β(E)]-6-[2-[2-(ethylmethylamino)-4-(4-fluorophenyl)-3-quinolinyl]ethenyl]tetrahydro-4-hydroxy-2H-pyran-2-one;
[4α,6β(E)]-6-[2-[2-(diethylamino)-4-(4-fluorophenyl)-3-quinolinyl]ethenyl]tetrahydro-4-hydroxy-2H-pyran-2-one;
[4α,6β(E)]-6-[2-[4-(4-fluorophenyl)-2-(1-pyrrolidinyl)-3-quinolinyl]ethenyl]tetrahydro-4-hydroxy-2H-pyran-2-one;
[4α,6β(E)]-6[2-[4-(4-fluorophenyl)-2-(1-piperidinyl)-3-quinolinyl]ethenyl]tetrahydro-4-hydroxy-2H-pyran-2-one;
[4α,6β(E)]-6-2-[4-(4-fluoropheny)-2-(4-morpholinyl)-3-quinolinyl]ethenyl]tetrahydro-4-hydroxy-2H-pyran-2-one;
[4α,6β(E)]-6-[2-[4-(4-fluorophenyl)-2-(4-thiomorpholinyl)-3-quinolinyl]ethenyl]tetrahydro-4-hydroxy-2H-pyran-2-one;
[4α,6β(E)]-6-[2-4-(4-fluorophenyl)-2-(1-piperazinyl-3-quinolinyl]ethenyl]tetrahydro-4-hydroxy-2H-pyran-2-one;
[4α,6β(E)]-6-[2-[4-(4-fluorophenyl)-2-(4-methyl-1-piperazinyl)-3-quinolinyl]ethenyl]-tetrahydro-4-hydroxy-2H-pyran-2-one;
[4α,6α]-6-[2-[2-(dimethylamino)-4-(4-fluorophenyl)-3-quinolinyl]ethyl]tetrahydro-4-hydroxy-2H-pyran-2-one;
[4α,6α]-6-2-[2-(ethylmethylamino)-4-(4-fluorophenyl)-3-quinolinyl]ethyl]tetrahydro-4-hydroxy-2H-pyran-2-one;
[4α,6α]-6-[2-[2-(diethylamino)-4-(4-fluorophenyl)-3-quinolinyl]ethyl]tetrahydro-4-hydroxy-2H-pyran-2-one;
4α,6α]-6-[2-[4-(4-fluorophenyl)-2-(1-pyrrolidinyl)-3-quinolinyl]ethyl]tetrahydro-4-hydroxy-2H-pyran-2-one;
[4α,6α]-6-[2-[4-(4-fluorophenyl)-2-(1-piperidinyl)-3-quinolinyl]ethyl]tetrahydro-4-hydroxy-2H-pyran-2-one;
[4α,6α]-6-[2-[4-(4-fluorophenyl)-2-(4-morpholinyl)-3-quinolinyl]ethyl]tetrahydro-4-hydroxy-2H-pyran-2-one;
[4α,6α]-6-[2-[4-(4-fluorophenyl)-2-(4-thiomorpholinyl)-3-quinolinyl]ethyl]tetrahydro-4-hydroxy-2H-pyran-2-one;
[4α,6α]-6-[2-[4-(4-fluorophenyl)-2-(1-piperazinyl)-3-quinolinyl]ethyl]tetrahydro-4-hydroxy-2H-pyran-2-one;
and [4α,6α]-6-2-[4-(4-fluorophenyl)-2-(4-methyl-1-piperazinyl)-3-quinolinyl]ethyl]tetrahydro-4-hydroxy-2H-pyran-2-one.

5. A pharmaceutical composition for inhibiting cholesterol biosynthesis comprising an effective amount of a compound as claimed in claim 1 in combination with a pharmaceutically acceptable carrier.

6. A method of inhibiting cholesterol biosynthesis in a patient in need of said treatment comprising administering a cholesterol synthesis inhibiting amount of a compound as defined by claim 1 in combination with a pharmaceutically acceptable carrier.

* * * * *